United States Patent [19]

Hock

[11] Patent Number: 5,510,370
[45] Date of Patent: Apr. 23, 1996

[54] PARATHYROID HORMONE AND RALOXIFENE FOR INCREASING BONE MASS

[75] Inventor: Janet M. Hock, Indianapolis, Ind.

[73] Assignee: Eli Lilly and Company, Indianapolis, Ind.

[21] Appl. No.: 400,436

[22] Filed: Mar. 6, 1995

Related U.S. Application Data

[63] Continuation of Ser. No. 96,480, Jul. 22, 1993, abandoned.

[51] Int. Cl.$^6$ .......... A61K 31/38; A61K 31/44; A61K 31/505; A61K 31/495
[52] U.S. Cl. .......... 514/443; 514/337; 514/257; 514/299; 514/249
[58] Field of Search .......... 514/337, 257, 514/299, 249, 443

[56] References Cited

U.S. PATENT DOCUMENTS

| | | | |
|---|---|---|---|
| 4,133,814 | 1/1979 | Jones et al. | 260/326.55 |
| 4,418,068 | 11/1983 | Jones | 424/267 |
| 5,118,667 | 6/1992 | Adams et al. | 514/12 |

OTHER PUBLICATIONS

Jordan et al, Effects of anti-estrogens on bone in castrated and intact female rats; Breast Cancer Research and Treatment; vol. 10; pp. 31–35 (1987).

Gunness-Hey, M. et al, Increased Trabecular Bone Mass in Rats Treated with Human Synthetic Parathyroid Hormone *Metab. Bone Dis. & Rel.* Res. 5, 177–181 (1984).

Hock, J. M. et al, Human Parathyroid Hormone–(1–34) Increases Bone Mass in Ovariectomized and Orchidectomized Rats* *Endocrinology*, vol. 122 No. 6 2899–2904 (1988).

Hock, J. M. et al., Comparison of the Anabolic Effects of Synthetic Parathyroid Hormone–Related Protein (PTHrP0 1–34 and PTH 1–34 on Bone in Rats* *Endocrinology* vol. 125 No. 4 2022–2027 (1989).

Gunness-Hey M. et al., Loss of the Anabolic Effect of Parathyroid Hormone on Bone after Discontinuation of Hormone in Rats, *Bone*, 10, 447–452 (1989).

Hock et al., Resorption Is Not Essential for the Stimulation of Bone Growth by hPTH–(1–34) in Rats In Vivo, *Journal of Bone and Mineral Research* vol. 4, No. 3, 449–458 (1989).

Hock J. M., et al. Effects of Continuous and Intermittent Administration and Inhibition of Resorption on the Anabolic Response of Bone to Parathyroid Hormone, *Journal of Bone and Mineral Research* vol. 7, No. 1 65–72 (1992).

Draper et al.. Effects of raloxifene (LY139481 HCl) on biochemical markers of bone and lipid metabolism in healthy postmenopausal women, Hong Kong, Fourth Int'l'. Symposium on Osteoporosis, Mar. 29, 1993.

*Primary Examiner*—Theodore J. Criares
*Attorney, Agent, or Firm*—James J. Sales

[57] ABSTRACT

The present invention includes a method for increasing bone mass in a subject by administration of PTH and raloxifene. Another aspect of the invention is a method for treating bone loss in a subject by administration of PTH and raloxifene. The invention further provides for a composition of PTH and raloxifene for increasing bone mass in a subject. Another aspect of the invention is a composition of PTH and raloxifene for treatment of bone loss in a subject.

12 Claims, No Drawings

5,510,370

PARATHYROID HORMONE AND RALOXIFENE FOR INCREASING BONE MASS

This application is a continuation of application Ser. No. 08/096,480, filed on Jul. 22, 1993, now abandoned.

FIELD OF THE INVENTION

The instant invention relates to the use of parathyroid hormone (PTH) for increasing bone mass when used with raloxifene. This therapeutic combination treatment results in an enhanced rate of bone formation and an increase in bone mass.

BACKGROUND OF THE INVENTION

Adams et al., U.S. Pat. No. 5,118,667, discloses the use of bone growth factors in combination with bone resorption inhibitors, either simultaneously in one composition or sequentially, to promote bone formation.

Slovik et al. (*J. Bone & Min. Res.* 1:377–381, 1986) report the stimulation of bone growth by parathyroid hormone (PTH).

Raloxifene is described in U.S. Pat. No. 4,418,068. In U.S. Patent application Ser. No. 07/920,933 filed Jul. 28, 1992 (X-7947), incorporated herein by reference, it is disclosed that raloxifene is useful in the inhibition or prevention of bone loss. Raloxifene has the following structure:

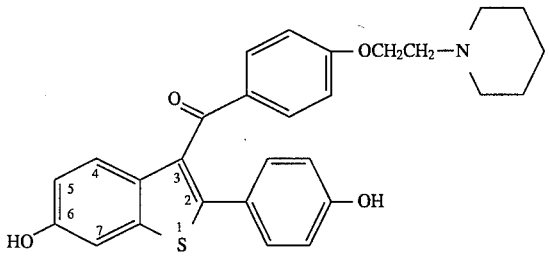

The present invention offers in vivo combination therapy for increasing bone mass through the administration of raloxifene and PTH. This combination provides more effective therapy for prevention of bone loss and replacement of bone than the components alone.

SUMMARY OF THE INVENTION

The present invention includes a method for increasing bone mass in a subject by administration of PTH and raloxifene.

Another aspect of the invention is a method for treating bone loss in a subject by administration of PTH and raloxifene.

The invention further provides for a composition of PTH and raloxifene for increasing bone mass in a subject.

Another aspect of the invention is a composition of PTH and raloxifene for treatment of bone loss in a subject.

DETAILED DESCRIPTION OF THE INVENTION

When raloxifene is refered to it is understood that it includes salts and solvates thereof. When PTH is refered to, it not only includes the complete human hormone but also includes portions which include the portion of the hormone responsible for bone growth promotion, such as PTH 1–34, and analogs in which the amino acid sequence is modified slightly however still retaining bone growth promotion properties, such as PTH-RP.

The term "inhibition of bone resorption" refers to prevention of bone loss, especially the inhibition of removal of existing bone either from the mineral phase and/or the organic matrix phase, through direct or indirect alteration of osteoclast formation or metabolism. Thus, the term "inhibitor of bone resorption" as used herein refers to agents that prevent bone loss by the direct or indirect alteration of osteoclast formation or metabolism.

The term "osteogenically effective" means that amount which effects the formation and differentiation of bone. As used herein, an osteogenically effective dose is also "pharmaceutically effective."

The term "subject" as used herein refers to a living vertebrate animal such as a mammal or bird in need of treatment, i.e., in need of bone repair or replacement. Such need arises locally in cases of bone fracture, non-union, defect, prosthesis implantation, and the like. Such need also arises in cases of systemic bone disease, as in osteoporosis, osteoarthritis, Paget's disease, osteomalacia, osteohalisteresis, multiple meyeloma and other forms of cancer, and age-related loss of bone mass.

The term "treatment" as used herein shall mean (1) providing a subject with an amount of a substance sufficient to act prophylactically to prevent the development of a weakened and/or unhealthy state; or (2) providing a subject with a sufficient amount of a substance so as to alleviate or eliminate a disease state and/or the symptoms of a disease state, and a weakened and/or unhealthy state.

Raloxifene may be made by established procedures, such as those detailed in U.S. Pat. No. 4,418,068. PTH may be synthetically or recombinantly prepared by established procedures. PTH 1–34 may be purchased from Bachem of Torrence, Calif.

Drugs which prevent bone loss, and/or add back lost bone and/or increase bone mass may be evaluated in the ovariectomized rat. This animal model is well established in the art (see, for example, Wronski, e al. (1985) *Calcif. Tissue Int* 37:324–328; Kimmel, et al. (1990) *Calcif Tissue Int* 46:101–110; and Durbridge, e t al. (1990) *Calcif. Tissue Int.* 47:383–387; these references were hereby incorporated in their entirety). Wronski, et al. ((1985) *Calcif. Tissue Int.* 43:179–183)) describe the association of bone loss and bone turnover in the ovariectomized rat. Also, Hock et al., describe the use of immature rats ((1988) *Endocrinology*, Vol. 122, pp. 2899–2904).

PTH and raloxifene may be administered sequentially, concurrently, or simultaneously as a single composition to the subject. If administered sequentially, the period between the administration of PTH and raloxifene will typically be one week to one year, and optimally, one week to six months. In a preferred administration scheme, the subject will, after administration of PTH, with or without raloxifene, be administered raloxifene after cessation of administration of PTH.

Pharmaceutical formulations of the invention which include PTH and/or raloxifene for administration will generally include an osteogenically effective amount of the bone growth factor to promote bone growth, in addition to a pharmaceutically acceptable excipient. Suitable excipients include most carriers approved for parenteral administration, including water, saline, Ringer's solution, Hank's solution, and solutions of glucose, lactose dextrose, ethanol, glycerol, albumin, and the like. These compositions may optionally include stabilizers, antioxidants, antimicrobials, preservatives, buffering agents, surfactants, and other accessory additives. PTH and/or raloxifene may also be delivered in an iontophoretic patch. A thorough discussion of suitable vehicles for parenteral administration may be found in E. W. Martin, "Remington's Pharmaceutical Sciences" (Mack Pub. Co., current edition sections relating to the excipient vehicles and formulating being incorporated herein by reference to disclose such). Such formulations are generally known to those skilled in the art and are administered systemically to provide systemic treatment.

If the combination is administered as a single composition, the molar ratio of PTH to raloxifene will be about 10:1 to 1:10, preferably, 5:1 to 1:5, and optimally, 1:1. Furthermore, if administered as a single composition, it may be separate components of the composition, or they may be conjugated to each other.

The precise dosage necessary will vary with the age, size, sex and condition of the subject, the nature and severity of the disorder to be treated, and the like; thus, a precise effective amount cannot be specified in advance and will be determined by the caregiver. However, appropriate amounts may be determined by routine experimentation with animal models. In general terms, an effective dose of PTH for systemic treatment will range from about 0.001 µg/kg to about 10 mg/kg of body weight, per day. As effective dose for raloxifene is about 0.001 mg/kg to 10 mg/kg of body weight, per day.

The methods and compositions of the invention are useful for treating bone fractures, defects, and disorders which result in weakened bones such as osteoporosis, osteoarthritis, Paget's disease, osteohalisteresis, osteomalacia, bone loss resulting from multiple myeloma and other forms of cancer, bone loss resulting from side effects of other medical treatment (such as steroids), and age-related loss of bone mass.

In accordance with one method of use, PTH and raloxifene may be administered systemically orally and/or parenterally, including subcutaneous or intravenous injection, and/or intranasally.

In accordance with another method of use PTH may be administered locally to a specific area in need of bone growth or repair, with the concomitant administration of raloxifene at the site, or the administration of raloxifene in a separate vehicle, or, it may be provided locally, with the administration of PTH in a separate vehicle. Thus, the PTH and/or raloxifene may be implanted directly at the site to be treated, for example, by injection or surgical implantation. Suitable carriers include hydrogels, controlled- or sustained-release devices (e.g., an Alzet® minipump), polylactic acid, and collagen matrices. Presently preferred carriers are formulations of atelopeptide collagen containing particulate calcium phosphate mineral components, such as combinations of homologous or xenographic fibrillar atelopeptide collagen (for example zyderm® Collagen Implant, available from Collagen Corporation, Palo Alto, Calif.) with hydroxyapatitetricalcium phosphate (HA-TCP, available from Zimmer, Inc., Warsaw, Ind.).

Dental and orthopedic implants can be coated with PTH in combination with raloxifene, to enhance attachment of the implant device to the bone. Alternatively, PTH can be used to coat the implant, and raloxifene can be administered concomitantly or sequentially in a separate vehicle, and vice versa.

In general, implant devices may be coated with a PTH and/or raloxifene as follows. The PTH (and raloxifene, if desired) is dissolved at a concentration in the range of 0.01 µg/ml to 200 mg/ml in phosphate-buffered saline (PBS) containing 2 mg/ml serum albumin. The porous end of an implant is dipped in the solution and is airdried (or lyophilized) or implanted immediately into the bony site. The viscosity of the coating solution is increased, if desired, by adding hyaluronate at a final concentration of 0.1 mg/ml to 100 mg/ml or by adding other pharmaceutically acceptable excipients. Alternatively, the solution containing PTH (and raloxifene, if desired) is mixed with collagen gel or human collagen (e.g. Zyderm® Collagen Implant, Collagen Corp., Palo Alto, Calif.) to a final collagen concentration of 2 mg/ml to 100 mg/ml to form a paste or gel, which is then used to coat the porous end of the implant device. The coated implant device is placed into the bony site immediately or is airdried and rehydrated with PBS prior to implanting, with the objective of maximizing new bone formation into the implant while minimizing the ingrowth of soft tissue into the implant site.

EXAMPLES

The following examples are put forth so as to provide those of ordinary skill in the art with a complete disclosure and description of how to use the compositions and methods of the invention and are not intended to limit the scope of what the inventors regard as their invention.

Rats were ovariectomized (OVX) 4 weeks of age and given sc vehicle (v) or hPTH 1–34 (P) at 8 µg/100 g/d alone or in combination with sc raloxifene (R) at 0.3 mg/100 g/d as follows: V 24d; R 24d; P24d; P&R 24d; P 12d then V12d; P 12d the R 12d; V12d; the R 12d. Rats were killed on d24, and blood, femurs, lumbar vertebrae and kidneys collected. Bone mass was measured as Ca and dry weight (DW) of distal half femurs; vertebrae were processed for histomorphometry.

As the final body weight of OVX rats given raloxifene was less than that of OVX or intact rats, data were corrected per 100 g body weight. Distal half femur Ca and DW was decreased by 15% in OVX compared to sham rats. Bone mass was increased by approximately 25% by raloxifene (R24d) and approximately 42% by PTH24d. The anabolic effect of PTH was lost following withdrawal (P12dV12d). Raloxifene had an additive effect when given concurrently with PTH (65% increase compared to OVX control). Femur length, serum Ca and kidney Ca were comparable between all groups.

|  |  | Final Body Wt. | Femur Length |
| --- | --- | --- | --- |
| Sham-vehicle (12d) | vehicle (12d) | 201 ± 4 | 28.6 ± 0.4 |
| OVX-vehicle (12d) | vehicle (12d) | 241 ± 5a | 28.8 ± 0.3 |
| OVX-PTH (12d) | PTH (12d) | 241 ± 4ac | 29.8 ± 0.2 |
| OVX-ralox (12d) | ralox (12d) | 189 ± 5b | 28.5 ± 0.2 |

| | | Final Body Wt. | Femur Length |
|---|---|---|---|
| OVX-PTH & ralox (12d) | PTH & Ralox (12d) | 190 ± 4b | 28.8 ± 0.2 |
| OVX PTH (12d) | Vehicle (12d) | 245 ± 4a | 29.6 ± 0.3 |
| OVX PTH (12d) | ralox (12d) | 208 ± 2bc | 30.0 ± 1.2 |
| OVX ralox (12d) | vehicle (12d) | 208 ± 6bc | 29.0 ± 0.3 |

Data expressed as mean ± sem for groups of 8 rats.
Significant difference, p < 0.05,
a vs sham-vehicle
c vs OVX ralox (12 + 12d)

Rats OVX at 4 weeks age and killed at approximately 10 weeks, gain weight more than intact rats of the same age. PTH does not modify this weight gain. Raloxifene prevents weight gain associated with OVX in the presence and absence of PTH. Rats given raloxifene for 12 days and then vehicle for the next 12 days showed less weight gain than OVX controls but more weight gain than rats continued on raloxifene.

Lack of effect on femur length, measure of longitude bone growth means that changes in body weight do not indicate changes in skeltal growth (rats just become leaner).

BONE MASS AS DRY WT OF DISTAL FEMURS

| | 1–12 | 13–24 | Total bone DW/100 g BW | Total bone Ca | Total bone DW |
|---|---|---|---|---|---|
| 1. Sham | V | V | 18.5 ± 0.5ab | 9.0 ± 0.4ab | 37.1 ± 0.8ab |
| 2. OVX | V | V | 15.8 ± 0.5abcd | 9.3 ± 0.5ab | 38.4 ± 1.4ab |
| 3. OVX | R | R | 19.7 ± 0.5ab | 9.6 ± 0.4ab | 37.1 ± 1.2ab |
| 4. OVX | P | P | 22.4 ± 0.4b | 12.2 ± 0.4 | 54.2 ± 1.7 |
| 5. OVX | P & R | P & R | 26.1 ± 0.9a | 11.6 ± 0.4 | 49.5 ± 2.0 |
| 6. OVX | P | V | 16.7 ± 0.3abc | 9.9 ± 0.3ab | 41.0 ± 1.0ab |
| 7. OVX | P | R | 17.8 ± 0.4abcd | 10.0 ± 0.7ab | 37.1 ± 1.0ab |
| 8. OVX | V | R | 16.8 ± 0.4abc | 9.0 ± 0.5ab | 34.9 ± 1.0ab | p < 0.05, a vs PTH; b vs PTHOR; c vs ralox; d vs OVX
V = vehicle
R = raloxifene
P = PTH
   Ca        DW = Total bone mass of distal femurs
% increase between means

| | | |
|---|---|---|
| 1. | –3% | –3% |
| 2. | | |
| 3. | 3% | 0% |
| 4. | 31% | 41% |
| 5. | 25% | 29% |
| 6. | 6% | 7% |
| 7. | 7% | –3% |
| 8. | –3% | –1% |

Total bone = sum of cortical and trabecular bone

Bone Mass of Distal Femurs

| | Trabecular Bone | | Cortical Bone |
|---|---|---|---|
| | Ca | DW | DW |
| Sham | 5.2 ± 0.2 | 9.7 ± 0.3 | 27.4 ± 0.6 |
| V | 4.7 ± 0.3 | 8.5 ± 0.5 | 29.9 ± 1.0 |
| P | 9.3 ± 0.5a | 16.5 ± 0.8 | 37.7 ± 1.5a |
| R | 5.6 ± 0.4 | 9.7 ± 0.5 | 27.5 ± 0.9 |
| P & R | 7.6 ± 0.6b | 13.4 ± 1.06 | 36.1 ± 1.46 |
| P–V | 5.6 ± 0.1 | 10.8 ± 0.4 | 30.2 ± 1.2 |
| P–R | 5.2 ± 0.3 | 9.1 ± 0.6 | 28.0 ± 0.7 |
| R–V | 4.3 ± 1.0 | 8.6 ± 0.5 | 26.3 ± 1.1 |

P < 0.05 a, b vs all other groups. Shows increases in both trabecular and cortical bone i.d Thus, the treatment of the ovariectomized rats with PTH resulted in increased bone formation. This increase, however, was significantly enhanced by concurrent treatment with raloxifene.

I claim:

1. A method for increasing bone mass in a subject, comprising administering a pharmaceutically effective dose of PTH and a pharmaceutically effective dose of raloxifene, to the subject.

2. The method of claim 1, wherein the subject is human.

3. The method of claim 1, wherein the administration is concurrent.

4. The method of claim 1, wherein PTH and raloxifene are administered simultaneously.

5. A method for treating bone loss in a subject, comprising administering a pharmaceutically effective dose of PTH and a pharmaceutically effective dose of raloxifene to the subject.

6. The method of claim 5 wherein the subject is human.

7. The method of claim 5 wherein the administration is concurrent.

8. The method of claim 5, wherein PTH and raloxifene are administered simultaneously.

9. A composition for increasing bone mass in a subject, comprising a pharmaceutically effective dose of PTH and a pharmaceutically effective dose of raloxifene in a pharmaceutically acceptable excipient.

10. The composition of claim 9 wherein the molar ratio of PTH to raloxifene is 10:1 to 1:10.

11. A composition for treating bone loss in a subject, comprising a pharmaceutically effective dose of PTH and a pharmaceutically effective dose of raloxifene in a pharmaceutically acceptable excipient.

12. The composition of claim 11 wherein the molar ratio of PTH to raloxifene is 10:1 to 1:10.

* * * * *